United States Patent [19]

Santi et al.

[11] Patent Number: 4,812,592

[45] Date of Patent: Mar. 14, 1989

[54] PROCESS FOR THE PREPARATION OF THE ESTERS OF AN ACID

[75] Inventors: Roberto Santi, Novara; Giuseppe Cometti, Verbania-Pallanza; Anselmo Pagani, Trecate, all of Italy

[73] Assignees: Istituto Guido Donegani, S.p.A., Novara; Consiglio Nazionale Delle Ricerche, Rome, both of Italy

[21] Appl. No.: 1,379

[22] Filed: Jan. 8, 1987

[30] Foreign Application Priority Data

Jan. 16, 1986 [IT] Italy ................................ 19097 A/86

[51] Int. Cl.$^4$ ............................................. C07C 69/66
[52] U.S. Cl. .................................. 560/180; 560/122; 560/123; 560/124; 560/126
[58] Field of Search ............... 560/180, 122, 123, 124, 560/126; 502/170

[56] References Cited

U.S. PATENT DOCUMENTS 3,997,593 12/1976 Stadler et al. ........................ 560/180
4,342,773 8/1982 Di Toro et al. ...................... 548/226

FOREIGN PATENT DOCUMENTS 56264 7/1982 European Pat. Off. ............ 560/180
2524222 1/1976 Fed. Rep. of Germany ...... 560/180
3316264 11/1984 Fed. Rep. of Germany ...... 560/180

OTHER PUBLICATIONS

Eskola et al., *Chemical Abstracts*, vol. 42, No. 122h, 1948.
White et al., *J. Am. Chem. Soc.*, vol. 106, pp. 3701–3703 (1984).

Primary Examiner—Bruce D. Gray
Attorney, Agent, or Firm—Bryan, Cave, McPheeters, McRoberts

[57] ABSTRACT

The invention concerns a process for the preparation of the esters of an alkyltartronic acid by direct oxidation, with $O_2$ or the like, at 30°–200° C., of the corresponding alkyl-malonic esters, in the presence of a catalytic system, comprising a salt of a transition metal, selected from Mn, Fe, Co and Cu, and an alkali-metal salt of an aliphatic carboxylic acid, optionally in the presence of a polar solvent.

26 Claims, No Drawings

PROCESS FOR THE PREPARATION OF THE ESTERS OF AN ACID

BACKGROUND OF THE INVENTION

It is known to prepare the esters of an alkyltartronic acids, having formula (I):

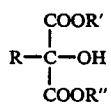

(I)

wherein R is an alkyl or cycloalkyl group and wherein R' and R", said groups being the same or different, are organic groups inert towards the reaction medium, by oxidation of the corresponding alkyl-malonic esters, having formula (II):

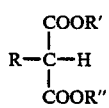

(II)

using, as an oxidizing agent, 98% $HNO_3$ (see U.S. Pat. No. 3,997,593). It is also known to perform the alkylation of mesoxalic esters, with a Cd-dialkyl compound or with trialkylphosphites (Arbuzov reaction).

Other methods teach how to prepare such esters by hydrolysis of meta-bromo-malonic acid with baryta and subsequent esterification with an alcohol, or by acidic alcoholysis of alpha-cyanolactic acid (pyruvic cyanohydrin) or of 2-acetoxy-2-methyl-malononitrile (1-acetoxy-1,1-dicyano-ethane).

A recent method, teaches how to prepare said esters by hydroxylating methacrylic acid to alpha-methylglyceric acid with $H_2O_2$, in the presence of $H_2WO_4$, and by subsequent oxidation to methyl-tartronic acid, using $HNO_3$ or $O_2$ in the presence of either Pd or Pt, followed by an esterification with a suitable alcohol.

The Applicant has now found that it is possible to obtain the alkyl-tartronic esters of formula (I), by direct oxidation of the alkyl-malonic esters of formula (II), without any toxic or dangerous oxidizing agent, such as, e.g., $HNO_3$, and without any use of noble metals, while performing extremely simple operations.

DISCLOSURE OF THE INVENTION

In its broadest aspect, the invention concerns a process for the preparation of esters of alkyl-tartronic acids having formula (I), by direct oxidation of the corresponding alkyl-malonic esters of formula (II), characterized in that the oxidation is carried out at 30°–200° C., with oxygen, air, or other $O_2$-containing gas, in the presence of a catalytic system comprising:

(a) an inorganic or organic salt of a transition metal selected from manganese, iron, cobalt and copper;
(b) an alkali-metal salt of an aliphatic carboxylic acid, in amounts from 0 to 60 moles per mole of transition metal;
optionally in the presence of a polar solvent having a dipolar moment equal to or higher than 1.68 Debye units.

The R' and R" substituents groups of formula (I) and (II) can be, e.g., alkyl groups containing from 1 to 6 C atoms, or cycloalkyl or aryl groups, optionally substituted.

The reaction can be performed under atmospheric pressure, with an oxygen (or air) flow rate of about 2 $m^3/h$ per $m^3$ of reaction volume, or under pressures ranging from 1 to 50 bar.

Salt (a) should be preferably selected from the salts of carboxylic acids and, among these, the acetates are preferred; particularly advantageous is the use of a cobalt salt in combination with a manganese salt in a molar ratio from 1:9 to 9:1 (expressed in terms of metal). Generally, amounts from 0.03 to 0.003 moles of transition metal per mole of alkyl-malonic ester can be used. The alkali-metal salt (b) can be preferably selected from sodium and potassium acetates and can be preferably used in amounts from 10 to 20 moles per mole of transition metal.

The polar solvent, in which also the catalyst should be soluble, can be preferably selected from the aliphatic carboxylic acids containing up to 5 C atoms; best results were obtained by using acetic acid.

The reaction temperature should generally be from 30° to 200° C., depending on the composition of the reaction mixture and on the desired reaction rate. The addition of at least 10% by weight of an alcohol, having from 2 to 6 C atoms, satisfactorily inhibits the cleavage of the alkyl-malonic ester used as the start product, thus promoting the recovery of the unreacted product. At the end of the reaction, the alkyl-tartronic ester can be stripped from the reaction mixture by conventional usual techniques, such as, e.g., distillation; it is also possible to recover the catalyst from the reaction mixture and to recycle same catalyst to the oxidation reactor. The process according to the invention, contrary to the processes heretofore used, allows alkyl-tartronic esters of formula (I) to be obtained with good yields, avoiding the use of noble metals and of either toxic or dangerous oxidizing agents, with good control of the reaction and by a very simple way, very suitable to be exploited on an industrial scale.

The esters having formula (I) are particularly useful when $R=CH_3$ and when $R'=R''=$alkyl groups having from 1 to 4 C atoms. In this case, they can be used, in fact, as intermediates for the preparation of aminoacids, of barbituric derivatives and of oxazolidinyl derivatives having pesticide or analgesic action; in particular, the di-ethyl ester of methyltartronic acid is an intermediate for the preparation of a fungicide known under the trade name "SERINAL".

Some Examples are now given for illustrative purposes, but are by no way limitative of the invention's scope.

EXAMPLE 1

We loaded into a glass reactor, equipped with stirrer, reflux condenser and temperature control system:
- 0.125 g (0.7 mmol) of $Co(CH_3COO)_2.4H_2O$;
- 0.125 g (0.7 mmol) of $Mn(CH_3COO)_2.4H_2O$;
- 0.75 g (9 mmol) of $NaOCOCH_3$;
- 5 g (28.7 mmol) of diethyl methylmalonate dissolved in 5 $cm^3$ of acetic acid, 1 $cm^3$ of water and 1 $cm^3$ of tertiary butyl alcohol.

We bubbled, through the mixture, 7 $dm^3/h$ of oxygen, while keeping the reaction mixture at 130° C. by means of an external oil bath. Five hours later, at the reaction end, the solvents were removed under vacuum and the residue was distilled under reduced pressure. A fraction was obtained, which contained 2.4 g of diethyl methylmalonate and 2.4 g of diethyl methyltartronate, which corresponds to a 52% conversion, an 84% selectivity to diethyl methyltartronate and thus a 43.9% yield.

EXAMPLE 2

We loaded into the same reactor, operating as in Example 1:
0.125 g (0.7 mmol) of Co(CH$_3$COO)$_2$.4H$_2$O;
0.125 g (0.7 mmol) of Mn(CH$_3$COO)$_2$.4H$_2$O;
0.75 g (9 mmol) of NaOCOCH$_3$;
5 g (28.7 mmol) of diethyl methylmalonate;
10 cm$^3$ of acetic acid;
1 cm$^3$ of water.
After the distillation we obtained:
2.45 g of diethyl methyltartronate;
0.72 g of diethyl methylmalonate;
0.4 g of residue;
which corresponds to an 85.6% conversion, a 52.4% selectivity and a 45% yield.

EXAMPLE 3

By repeating the conditions of Examples 1 and 2, we loaded:
0.125 g (0.7 mmol) of Mn(CH$_3$COO)$_2$.4H$_2$O;
0.125 g (0.7 mmol) of Co(CH$_3$COO)$_2$.4H$_2$O;
0.75 g (9 mmol) of NaOCOCH$_3$;
5 g (28.7 mmol) of diethyl methylmalonate;
10 cm$^3$ of acetic acid;
After the distillation we obtained:
2.7 g of diethyl methyltartronate;
0.27 g of diethyl methylmalonate;
0.7 g of residue;
which corresponds to a 94.6% conversion, a 52.3% selectivity and a 49.5% yield.

What is claimed is:

1. A process for the preparation of esters of an alkyl-tartronic acid, said esters having the formula (I):

$$\underset{\underset{\text{COOR''}}{|}}{\overset{\overset{\text{COOR'}}{|}}{R-C-OH}} \quad (I)$$

wherein R is an alkyl or cycloalkyl group and wherein R' and R'' are C$_1$-C$_6$ alkyl, by direct oxidation of the corresponding alkyl-malonic ester having the formula (II):

$$\underset{\underset{\text{COOR''}}{|}}{\overset{\overset{\text{COOR'}}{|}}{R-C-H}} \quad (II)$$

wherein R, R' and R'' are as above defined, characterized in that the oxidation is carried out at 30°-200° C. in the presence of an oxygen-containing gas and with a catalytic system comprising:
(a) an inorganic or organic salt of a transition metal selected from the group consisting of manganese, iron, cobalt and copper; and
(b) an alkali-metal salt of an aliphatic carboxylic acid in a catalytic amount not greater than 60 moles per mole of transition metal.

2. A process according to claim 1, wherein also an aliphatic alcohol having from 2 to 6 C atoms is present, in amounts up to 50% by weight, with respect to the alkyl-malonic ester to be oxidized.

3. A process according to claim 1 wherein the salt of said transition metal is a salt of a mono-carboxylic aliphatic acid.

4. A process according to claim 3, wherein said salt is an acetate of Mn, Fe, Co or Cu.

5. A process according to claim 1, wherein a cobalt salt is used, in combination with a manganese salt, in a molar ratio, expressed in terms of metal, from 1:9 to 9:1.

6. A process according to claim 1, wherein an amount from 0.03 to 0.003 moles of transition metal per mole of alkyl-malonic ester is used.

7. A process according to claim 1, wherein from 10 to 20 moles of alkali-metal salt per mole of transition metal are used.

8. A process according to claim 1, wherein the alkali-metal salt is selected from sodium acetate and potassium acetate.

9. A process according to claim 1, wherein the solvent is selected from the group consisting of aliphatic carboxylic acids containing up to 5 C atoms.

10. A process according to claim 9, wherein the solvent is acetic acid.

11. A process according to claim 1, wherein an aliphatic alcohol, containing from 2 to 6 C atoms, is added to the reaction mixture.

12. A process according to claim 11, wherein said alcohol is tert-butanol.

13. A process according to claim 10, wherein the acetic acid is in admixture with H$_2$O.

14. A process according to claim 1, wherein R is methyl and wherein R' and R'' are C$_1$-C$_4$ alkyl.

15. A process according to claim 1, wherein a polar solvent having a dipolar moment equal to or higher than 1.68 Debye units is present in the reaction mixture.

16. A process for the preparation of esters of an alkyl-tartronic acid, said esters having the formula (I):

$$\underset{\underset{\text{COOR''}}{|}}{\overset{\overset{\text{COOR'}}{|}}{R-C-OH}} \quad (I)$$

wherein R is an alkyl or cycloalkyl group and wherein R' and R'' are C$_1$-C$_6$ alkyl, by direct oxidation of the corresponding alkyl-malonic ester having the formula (II):

$$\underset{\underset{\text{COOR''}}{|}}{\overset{\overset{\text{COOR'}}{|}}{R-C-H}} \quad (II)$$

wherein R, R' and R'' are as above defined, characterized in that the oxidation is carried out at 30°-200° C. in the presence of an oxygen-containing gas and with a catalytic system consisting essentially of an organic salt of a transition metal selected from the group consisting of manganese, iron, cobalt, and copper.

17. A process according to claim 16, wherein the salt of said transition metal is a salt of a mono-carboxylic aliphatic acid.

18. A process according to claim 17, wherein said salt is an acetate of manganese, iron, cobalt, or copper.

19. A process according to claim 16, wherein a cobalt salt in combination with a manganese salt are used at a molar ratio of from 1:9 to 9:1 expressed in terms of metal.

20. A process according to to claim 16, wherein an amount from 0.03 to 0.003 moles of transition metal per mole of alkyl-malonic ester is used.

21. A process according to claim 16, wherein a polar solvent having a dipolar moment equal to or higher than 1.68 Debye units is present in the reaction mixture.

22. A process according to claim 21, wherein the solvent is acetic acid.

23. A process according to claim 16, wherein an aliphatic alcohol containing from 2 to 6 carbon atoms is added to the reaction mixture.

24. A process according to claim 23, wherein said alcohol is tert-butanol.

25. A process according to claim 22, wherein the acetic acid is in admixture with $H_2O$.

26. A process according to claim 16, wherein R is methyl and wherein R' and R" are $C_1$-$C_4$ alkyl.

* * * * *